(12) United States Patent
Oddos

(10) Patent No.: US 8,877,820 B2
(45) Date of Patent: Nov. 4, 2014

(54) COMPOSITIONS COMPRISING A RETINOID AND AN NFKB-INHIBITOR AND THEIR METHODS OF USE

(71) Applicant: Johnson & Johnson Consumer Companies, Inc., Skillman, NJ (US)

(72) Inventor: Thierry Oddos, Meudon (FR)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 13/773,768

(22) Filed: Feb. 22, 2013

(65) Prior Publication Data

US 2013/0165512 A1 Jun. 27, 2013

Related U.S. Application Data

(62) Division of application No. 12/911,038, filed on Oct. 25, 2010.

(51) Int. Cl.

| | | |
|---|---|---|
| *A61K 31/07* | (2006.01) | |
| *A61K 31/045* | (2006.01) | |
| *A61K 8/67* | (2006.01) | |
| *A61K 31/277* | (2006.01) | |
| *A61K 8/34* | (2006.01) | |
| *A61Q 19/00* | (2006.01) | |
| *A61Q 19/08* | (2006.01) | |
| *A61K 8/46* | (2006.01) | |
| *A61K 8/97* | (2006.01) | |
| *A61K 45/06* | (2006.01) | |

(52) U.S. Cl.
CPC ............... *A61K 31/07* (2013.01); *A61K 8/671* (2013.01); *A61K 31/277* (2013.01); *A61K 8/347* (2013.01); *A61Q 19/00* (2013.01); *A61Q 19/08* (2013.01); *A61K 2800/782* (2013.01); *A61K 8/46* (2013.01); *A61K 8/97* (2013.01); *A61K 45/06* (2013.01)
USPC .......................................... 514/725; 514/730

(58) Field of Classification Search
USPC .................................................. 514/725, 730
See application file for complete search history.

(56) References Cited

U.S. PATENT DOCUMENTS

| | | | |
|---|---|---|---|
| 4,337,370 A | 6/1982 | Takisawa et al. | |
| 7,442,391 B2 | 10/2008 | Koganov | |
| 7,473,435 B2 | 1/2009 | Koganov | |
| 7,537,791 B2 | 5/2009 | Koganov | |
| 2009/0263513 A1 | 10/2009 | Marini | |
| 2012/0101156 A1 | 4/2012 | Oddos | |

FOREIGN PATENT DOCUMENTS

| | | | |
|---|---|---|---|
| WO | WO 01/89502 A2 | 11/2001 | |
| WO | WO 2008/148016 A | 12/2008 | |
| WO | WO 2010/072787 A2 | 7/2010 | |

OTHER PUBLICATIONS

Akerlof, "Dielectric Constants of Some Organic Solvent-Water Mixtures at Various Temperatures," JACS, Nov. 1932, vol. 54, No. 11, p. 4125-4139.
Product Scan Information: Jan Marini Age Intervention Enlighten, 2008/2009.
Product Scan Information: Kinerase—Brightening Anti-Aging System, 2008/2009.
Database GNPD [online] Mintel; Jun. 30, 2008, "Enlighten Facial Lotion", XP002708108, Database accession No. 925294, Abstract.

*Primary Examiner* — Renee Claytor
(74) *Attorney, Agent, or Firm* — Sharon E. Hayner

(57) ABSTRACT

A composition including a retinoid, an NFκB-inhibitor, and a cosmetically-acceptable topical carrier is provided. Methods of treating the skin are also provided.

5 Claims, No Drawings

COMPOSITIONS COMPRISING A RETINOID AND AN NFKB-INHIBITOR AND THEIR METHODS OF USE

CROSS-REFERENCE TO RELATED APPLICATIONS

This application is a divisional of U.S. patent application Ser. No. 12/911,038 filed Oct. 25, 2010, the disclosure of which is hereby incorporated by reference in its entirety.

FIELD OF THE INVENTION

A composition comprising a retinoid, an NFκB-inhibitor and a cosmetically acceptable topical carrier is provided. The composition is useful for topical application to the skin.

BACKGROUND OF THE INVENTION

Retinoids are known to treat different skin conditions such as acne or photo-aging. However retinoids used for topical application, such as retinoic acid, retinaldehyde or retinol can, in certain instances result in redness, itching, stinging, skin scaling or other manifestations of irritation. The inventors have considered that a possible solution to decrease irritation is to use lower concentrations of retinoids in the topical composition. However compositions with reduced levels of retinoids can, understandably, have reduced efficacy.

The inventors have now surprisingly discovered that a particular class of anti-inflammatory compounds, agents that inhibit the cell transcription factor, nuclear kappa-B (NFκB) can be combined with retinoids in a manner to provide a surprisingly large and unexpected synergistic boost in retinol activity, as measured by the expression of the CRAPBII gene.

SUMMARY OF THE INVENTION

In one aspect, the invention provides a composition comprising a retinoid, an NFκB-inhibitor, and a cosmetically-acceptable topical carrier, wherein the amount of retinoid in the composition is no more than about 0.075% by weight of the composition.

In another aspect, the invention provides a method of treating skin that includes topically applying the above composition to mammalian skin.

Other features and advantages of the present invention will be apparent from the detailed description of the invention and from the claims.

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Unless otherwise indicated, an amount, percentage, or concentration refers to an amount, percentage, or concentration by weight (i.e., % (W/W). Unless stated otherwise, all ranges are inclusive of the endpoints, e.g., "from 4 to 9" includes the endpoints 4 and 9.

As used herein, "topically applying" means directly laying on or spreading on outer skin, the scalp, or hair, e.g., by use of the hands or an applicator such as a wipe, roller, or spray.

As used herein, "cosmetically acceptable" means that the ingredients the term describes are suitable for use in contact with tissues (e.g., the skin or hair) without undue toxicity, incompatibility, instability, irritation, allergic response, or the like.

As used herein, the term "treating" or "treatment" means the treatment (e.g., alleviation or elimination of symptoms and/or cure) and/or prevention or inhibition of the condition (e.g., a skin condition).

Compositions of the present invention are suitable for treating mammalian skin, for example for improving various signs of skin aging, such as firmness, texture, or the appearance of wrinkles. As used herein, "skin in need of improving the signs of aging" means a skin that is, but not limited to, sagging, loose, lax, rough, wrinkly, thinned, or uneven. Improving the signs of aging means improving the firmness of the skin, improving the texture of the skin, improving the appearance of lines or wrinkles in skin, improving the skin tone, or the treatment of external aggressions in skin.

As used herein, "improving the firmness of skin" means the enhancing of the firmness or elasticity of the skin, preventing the loss of firmness or elasticity of skin, or preventing or treating sagging, lax and loose skin. The firmness or elasticity of the skin can be measured by use of a cutometer. See *Handbook of Non-Invasive Methods and the Skin*, eds. J. Serup, G. Jemec & G. Grove, Chapter 66.1 (2006). The loss of skin elasticity or firmness may be a result of a number of factors, including but not limited to aging, disease, hormonal changes, trauma, environmental damage, or the result of an application of cosmetics to the skin.

As used herein, "improving the texture of skin" means the smoothing of the surface of the skin to remove either bumps or crevasses on the skin surface.

As used herein, "improving the appearance of lines or wrinkles in skin" means preventing, retarding, arresting, or reversing the process of wrinkle and fine line formation in skin.

As used herein, "treatment of external aggressions in skin" means the reduction or prevention of the damage from external aggressions in skin. Examples of external aggressions include, but are not limited to, damage to the skin from the use of cleansers (e.g., topical cleansers containing surfactants), make-up, shaving as well as environmental damage such as from UV light (e.g., sun damage from sunlight or damage from non-natural sources such as UV lamps and solar simulators), ozone, exhaust, pollution, chlorine and chlorine containing compounds, and cigarette smoke. Effects of external aggressions on the skin include, but are not limited to, oxidative and/or nitrosative damage to and modifications on lipids, carbohydrates, peptides, proteins, nucleic acids, and vitamins. Effects of external aggressions on the skin also include, but are not limited to, loss of cell viability, loss or alteration of cell functions, and changes in gene and/or protein expression.

As used herein, the term "lightening the skin" refers generally to lightening, brightening, whitening, and/or evening of the skin tone, skin color, and/or shade of skin, and/or to the reduction in sallowness, and/or to the lightening and/or fading of hyperpigmented marks and/or lesions including, but not limited to, pigmented spots, melanin spots, age spots, sun spots, senile lentigos, freckles, lentigos simplex, pigmented solar keratosis, seborrhoeic keratosis, melasma, acne marks, post-inflammatory hyperpigmentation, lentigines, ephelides, combinations of two or more thereof and the like. In certain embodiments, "lightening the skin" also refers to increased skin radiance, glow, translucency and/or luminescence and/or obtaining a more radiant, glowing, translucent or luminous skin tone appearance or a less yellow or sallow skin tone. In certain preferred embodiments, "lightening the skin" refers to lightening and evening the skin tone, increasing skin radiance and/or lightening age spots.

As used herein, the term "skin in need of skin lightening treatment" refers generally to skin that exhibits one or more property selected from the group consisting of: skin having a measured Individual Typology Angle (ITA) value below 41 as determined per the COLIPA GUIDELINE: GUIDELINE FOR THE COLORIMETRIC DETERMINATION OF SKIN COLOUR TYPING AND PREDICTION OF THE MINIMAL ERYTHEMAL DOSE (MED) WITHOUT UV EXPOSURE published in 2007, which is incorporated herein by reference and further described below, darkened and/or sallow skin, including skin darkened by UV, skin with uneven skin tone, or skin with one or more hyperpigmented marks and/or lesions including, but not limited to, pigmented spots, melanin spots, age spots, sun spots, senile lentigos, freckles, lentigos simplex, pigmented solar keratosis, seborrhoeic keratosis, melasma, acne marks, post-inflammatory hyperpigmentation, lentigines, ephelides, combinations of two or more thereof and the like. In the COLIPA guidelines, skin color is defined function of the ITA value as: very light skin>55; Light skin 41-55, Intermediate 28-41, and Tan skin<28. In certain preferred embodiments, "skin in need of skin lightening" refers to individuals with a skin having an ITA value of less than 41, such as about 40 or less, about 35 or less, about 30 or less, or more preferably about 28 or less. In certain other preferred embodiments, the present invention is directed to compositions and methods for use on skin in need of skin lightening treatment selected from sallow and/or darkened skin. In certain other preferred embodiments, the present invention is directed to compositions and methods for use on skin in need of skin lightening treatment selected from the group consisting of age spots, freckles, marks left after acne, and combinations of two or more thereof.

Compositions of the present invention are also suitable for treating acne. As used herein, "treating acne" refers to a mitigating, reducing, preventing, improving, or eliminating the presence or signs of disorders resulting from the actions of hormones and other substances on the sebaceous glands and hair follicles, typically leading to clogged pores and the formation of inflammatory or non-inflammatory lesions on the skin. Specifically, it relates to the treatment or prevention of blemishes, lesions, or pimples, pre-emergent pimples, blackheads, and/or whiteheads. As used herein, a "pre-emergent pimple" is an inflamed follicle that are not visually apparent on the surface of the skin with the naked eye (e.g., as a lesion).

As used herein, "cosmetic" refers to a beautifying substance or preparation which preserves, restores, bestows, simulates, or enhances the appearance of bodily beauty or appears to enhance the beauty or youthfulness, specifically as it relates to the appearance of tissue or skin.

As used herein, "cosmetically effective amount" means an amount of a physiologically active compound or composition sufficient for treating one or more signs of skin aging or acne, but low enough to avoid serious side effects. The cosmetically effective amount of the compound or composition will vary with the particular condition being treated, the age and physical condition of the end user, the severity of the condition being treated/prevented, the duration of the treatment, the nature of other treatments, the specific compound or product/composition employed, the particular cosmetically-acceptable carrier utilized, and like factors.

Retinoid

Compositions of the present invention include at least one retinoid. As used herein, "retinoid" means a compound from a class of compounds structurally similar to Vitamin A, such as those characterized by the structure below:

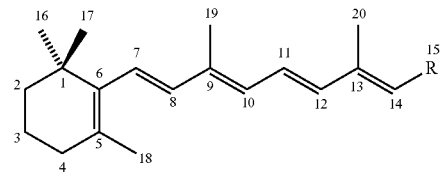

wherein R represents a functional group such as $CH_2OH$ (retinol), CHO (retinal), $CO_2H$ (retinoic acid), $CH_2OCOCH$ (retinyl acetate). Other derivatives are suitable as well, e.g. other esters such as retinyl palmitate, amine derivatives, and the like. In one embodiment, the retinoid is selected from retinol, retinal, retinoic acid, retinyl acetate, and retinyl palmitate. In a preferred embodiment, the retinoid is retinol.

The inventors have found that retinoid levels can be maintained at relatively low levels in the composition, yet provide a surprisingly larger than expected efficacy. In certain embodiments of the invention, the amount of retinoid (e.g., retinol) in the composition is no more than about 0.075% by weight of the composition (e.g., no more than about 0.0026 moles per liter of composition or no more than about 247,500 International Units of Vitamin A per 100 grams of composition). In certain embodiments, the amount of retinoid in the composition is from about 0.01% to about 0.075% by weight of the composition (e.g., from about 0.000349 to about 0.0026 moles per liter of composition), such as from about 0.01% to about 0.06% by weight of the composition (e.g., from about 0.000349 to about 0.00209 moles per liter of composition). In a preferred embodiment, the composition comprises retinol in the above concentration ranges.

NFκB-Inhibitor

Compositions of the present invention include at least one NFκB-inhibitor. As used herein, "NFκB-inhibitor" means a compound that inhibits the cell transcription factor nuclear kappa-B (NFκB). In one embodiment, the NFκB-inhibitor, when tested according to the NFκB-INHIBITION TEST as defined below, has a Percent NFκB Inhibition of at least about 35%, preferably at least about 55%, more preferably at least about 70%, most preferably at least about 90%, when tested at a concentration that is preferably from 1 microgram per milliliter to about 100 micrograms per milliliter. That is, the compound demonstrates the recited Percent NFκB Inhibition at at least one concentration in the range of 1 microgram per milliliter to 100 micrograms per milliliter. The compound need not provide the recited Percent NFκB Inhibition at all concentrations from 1 microgram per milliliter to 100 micrograms per milliliter, but provides the recited Percent NFκB Inhibition at at least one concentration in this range.

In a preferred embodiment, the NFκB-inhibitor has a Percent NFκB Inhibition of at least about 35%, preferably at least about 55%, more preferably at least about 70%, most preferably at least about 90%, when tested at a concentration of 10 micrograms per milliliter.

The NFκB-INHIBITION TEST is conducted in the following manner. FB293 cells, a stable transfected human epithelial cell line containing the gene reporter for NF-κB are used. They may be obtained from, e.g., Panomics (Fremont, Calif.). FB293 are plated at a density of $5 \times 10^4$ cells/mL in a suitable medium, e.g., Dulbecco's modified Eagle's medium (DMEM) supplemented with 10% fetal bovine serum (Invitrogen, San Diego, Calif.). The FB293 cells are stimulated with 100 ng/mL of Tumor Necrosis Factor-α (TNFα, available from Sigma-Aldrich of St Louis, Mo.) in the presence of the test sample. Separately, a control sample is tested wherein no test sample is applied. Following a 24-hour incubation at 37° C. with 5% $CO_2$, cells are lysed with 40 µl of reporter lysis buffer (Promega, Madison, Wis.). A 20-µl aliquot of the lysate is assayed using a luciferase assay kit (Promega) and counted for 10 s in a Lmax luminometer (Molecular Devices, Sunnyvale, Calif.) with the data represented as the relative light unit/second. Percent NFκB Inhibition of the test sample is calculated as:

NFκB Inhibition=$[1-(L_{sample}/L_{control})]*100$ where $L_{sample}$ is the luminescence of the sample and $L_{control}$ is the luminescence of the control.

In one embodiment, the NFκB-inhibitor is selected from the group consisting of the following compounds: substituted resorcinols, (E)-3-(4-methylphenylsulfonyl)-2-propenenitrile (such as "Bay 11-7082," commercially available from Sigma-Aldrich of St. Louis, Mo.), tetrahydrocurcuminoids (such as Tetrahydrocurcuminoid CG, available from Sabinsa Corporation of Piscataway, N.J.), extracts of *Paulownia tomentosa* wood and combinations thereof. In another embodiment, the NFκB-inhibitor is selected from the group consisting of substituted resorcinols, tetrahydrocurcuminoids, and combinations thereof.

In one embodiment, the NFκB-inhibitor comprises an extract of *Paulownia tomentosa* wood. *Paulownia* is a genus of plants native to Asia which has spread gradually to Europe and the USA. In Japan, *Paulownia* is called kiri which refers specifically to one species, *Paulownia tomentosa*, also called "Princess Tree." Other names which are commonly used are "empress tree", "Foxglove Tree", "Royal *Paulownia*", "Pao tong" (in China) and "Odong-Namoo" (in Korea). The scientific name is "*Paulownia tomentosa*" with a number of synonyms reported in various literature, i.e. "*Paulownia imperialis*", "*Paulownia recurva*", and "*Bignonia tomentosa*". *Paulownia tomentosa* belongs to the family "*Paulowniaceae*" or sometimes refer to "*Scrophulariaceae*". The United States Department of Agriculture (plants.USDA.gov) Plant database identifies Princess tree by a unique symbol "PATO2", with *Paulownia tomentosa* and *Paulownia imperialis* as synonym names.

Any suitable extracts of *Paulownia tomentosa* wood may be used. In general, the wood of the *Paulownia tomentosa* tree includes wood from the stem, branches, or a combination of both. Suitable extracts of *Paulownia tomentosa* wood may be derived from wood chips, wood dusts and/or small cuttings, and the like.

Suitable extracts of *Paulownia tomentosa* wood may be obtained using conventional methods including, but not limited to, direct extraction of material from the wood by grinding, macerating, pressing, squeezing, mashing, centrifuging, and/or processes such as cold percolation, agitation/distillation, microwave assisted extraction, sonication, supercritical/subcritical $CO_2$ compressed gas extraction with or without polar modifiers, pressurized solvent extraction, accelerated solvent extraction, pressurized or normal hot water extraction, surfactant assisted pressurized hot water extraction, oil extraction, membrane extraction, Soxhlet extraction, the gold finger distillation/extraction and/or processes disclosed, for example, in U.S. Pat. Nos. 7,442,391, 7,473,435, and 7,537,791 to Integrated Botanical Technologies, LLC, incorporated herein by reference, and the like, or by other methods such as solvent extraction, and the like. Any of a variety of solvents including polar solvents, non-polar solvents, or combinations of two or more thereof may be used in methods of comprising solvent extraction. Suitable polar solvents include polar inorganic solvents such as water and the like, polar organic solvents such as alcohols and corresponding organic acids, for example $C_1$-$C_8$ alcohols including methanol, ethanol, propanol, butanol, and the like and organic acids, including acetic acid, formic acid, propanoic acid, and the like, polyols and glycols, including $C_1$-$C_8$ polyols/glycols and the like, and combinations of two or more thereof. Suitable non-polar solvents include non-polar organic solvents such as alkanes, including $C_1$-$C_8$ alkanes, cycloalkanes, including $C_1$-$C_8$ alkanes, alkyl ethers, including $C_1$-$C_8$ alkyl ethers, Petroleum ethers, ketones, including $C_1$-$C_8$ ketones, methylene chloride, ethyl acetate, xylene, toluene, chloroform, vegetable oil, mineral oil and the like. In another embodiment extraction may be obtained by non-polar solvents described above or supercritical fluid extraction with or without a polar modifier such as $C_1$-$C_8$ alcohols, water, $C_1$-$C_8$ polyols/glycols or $C_1$-$C_8$ organic acids. In certain preferred embodiments, the extract of the invention is a polar extract prepared by pulverizing the wood and extracting using a polar solvent having a dielectric constant value of between 1 and 100 at 20° C., preferably a dielectric constant of a value between 4 and 60 at 20° C., more preferably a dielectric constant of a value between 4 and 50 at 20° C., and even more preferably a dielectric constant of a value between 4 and 40 at 20° C. Examples of preferred polar solvents include $C_1$-$C_8$ alcohols, $C_1$-$C_8$ polyols/glycols, $C_1$-$C_8$ organic acids, water and combinations of two or more thereof having a dielectric constant value of between 1 and 100, preferably between 4 and 60, and more preferably between 5 and 40 at 20° C., including, but not limited to, those solvents and combinations of solvents having the desired dielectric constant value as disclosed in "Dielectric Constants of Some Organic Solvent-Water Mixtures at Various Temperatures," Akerlof, Gosta; *JACS*, Vol. 54, No. 11 (November 1932), pp. 4125-4139, incorporated herein by reference. In certain preferred embodiments, the polar extract is extracted using one or more $C_1$-$C_8$ alcohols, $C_1$-$C_8$ polyols, $C_1$-$C_8$ glycols, and combinations of two or more thereof. In certain more preferred embodiments, the extract is extracted using one or more $C_1$-$C_4$ alcohols, $C_1$-$C_4$ polyols, and/or $C_1$-$C_4$ glycols. In certain more preferred embodiments, the extract is prepared using a solvent comprising methanol, ethanol, or a combination thereof with or without presence of water. In more preferred embodiment, the extract is prepared using anhydrous alcohol or reagent grade denatured alcohol and dried Kiri wood dust agitating at room temperature for 3 days. In certain preferred embodiments, the extract may be further refined by charcoal (also referred to as active carbon) treatment.

In certain embodiments, the *Paulownia tomentosa* extract may be prepared to be essentially free of certain materials. In one embodiment, the extract is essentially free of Ursolic acid, beta-Sitosterol, or both.

In certain embodiments, the composition may additionally include extracts from other parts of *Paulownia tomentosa*, for example, one or more of the bark, leaves, roots, fruits, seeds, or flowers. In other embodiments, the composition is essentially free from extracts of other non-wood parts of *Paulownia tomentosa*.

In a preferred embodiment, the NFκB-inhibitor is a substituted resorcinol. Resorcinol is a dihydroxy phenol compound (i.e., 1,3 dihydroxybenzene) having by the following structure:

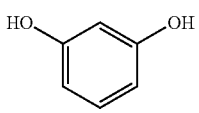

As used herein, "substituted resorcinol" means resorcinol comprising at least one substituent in the 2, 4, 5, or 6 position. Thus, the substituted resorcinol may have as few as one and as many as four substituents. Positions 1 and 3 of the substituted resorcinol comprise —OH groups, as shown above.

It is highly preferred that all of the substituents of the substituted resorcinol are free of phenyl (—C6H5 aromatic) moieties. In certain embodiments, all of the substituents are free of aromatic moieties (with or without heteroatoms).

In another embodiment, it is preferred that all of the substituents of the substituted resorcinol are free of ketone functionalities (carbonyls bonded to two other carbon atoms).

In certain preferred embodiments, all of the substituents of the substituted resorcinol are free of both phenyl functionalities and ketone functionalities.

In certain preferred embodiments, the substituted resorcinol comprises at least one substituent comprising 5 to 11 carbon atoms, preferably 5 to 10 carbon atoms, more preferably 5 to 9 carbon atoms, most preferably 5 to 8 carbon atoms. In certain other embodiments, at least one substituent comprises an alkyl group, such as one having the number of carbon atoms described above. The alkyl group is preferably unsaturated.

In certain embodiments, the 4 position of the resorcinol is substituted, and, in certain embodiments, only the 4 position is substituted. In another embodiment, the 4 position is substituted with an akyl group. In certain preferred embodiments, the substituted resorcinol comprises a single substituent at the 4 position that comprises an alkyl group. In certain other preferred embodiments, the substituted resorcinol comprises a single substituent at the 4 position that consists of an alkyl group directly bonded to the benzene ring.

Particularly suitable substituted resorcinols include 4-hexyl resorcinol and 4-octylresorcinol, particularly 4-hexyl resorcinol. The structures of 4-hexylresorcinol and 4-octylresorcinol are shown below:

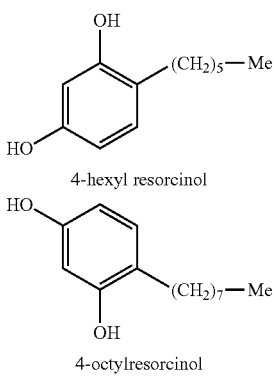

4-Hexyl resorcinol is commercially available as "SYNOVEA HR" from Sytheon of Lincoln Park, N.J. 4-Octylresorcinol is commercially available from City Chemical LLC of West Haven, Conn.

In certain embodiments, the substituted resorcinol comprises at least two substituents in the 2, 4, 5, or 6 positions. Such substituents may optionally be linked to form a ring, such as a cyclic aliphatic hydrocarbon optionally comprising heteroatoms such as sulfur or oxygen. Such a linked substituent may comprise 5 to 10 carbon atoms, e.g., 8 to 10 carbon atoms, and optionally include 1 to 3 heteroatoms. Examples of suitable substituted resorcinols comprising cyclic aliphatic substituents joining the 2 and 3 positions include Zearalanone and β-Zearalanol:

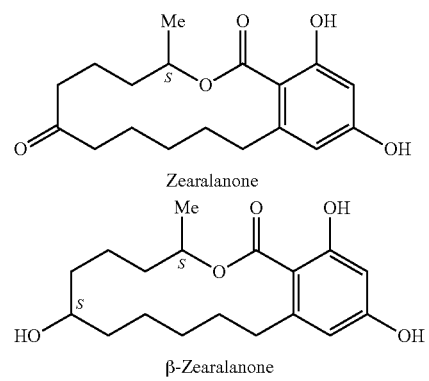

Zearalanone and β-Zearalanol are commercially available from Sigma Chemicals of St. Louis, Mo.

In certain other embodiments, the substituted resorcinol comprises halide-containing and/or nitroso-containing substituents. Suitable examples contain —Cl or —N=O bonded directly to the benzene ring. These substituents may exist for example in the 2 and 4, 2 and 6, or 4 and 6 positions. An example of a dihalide-substituted resorcinol is 2,6-dichlororesorcinol. An example of a dinitroso-substituted resorcinol is 2,4-dinitrososorcinol:

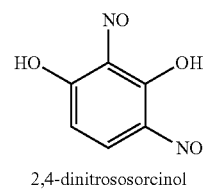

2,4-dinitrososorcinol 2,6-Dichlororesorcinol and 2,4-Dinitrososorcinol are available from City Chemical LLC of West Haven, Conn.

Substituted resorcinols are prepared by means known in the art, for example, using techniques described in U.S. Pat. No. 4,337,370, the contents of which are incorporated herein by reference.

The substituted resorcinols may have any suitable molecular weight. In certain embodiments, the molecular weight of the substituted resorcinol ranges between about 175 and about 300.

CRAPBII Expression

In one embodiment of the invention, the concentration of NFκB-inhibitor in the composition is selected to provide, in combination with the retinoid, at least about a 15% synergy in CRAPBII expression as measured by the CRAPBII EXPRESSION TEST, described below. Such a combination advantageously allows for the use of relatively low levels of retinoids, which are sometimes irritating, while maintaining a high degree of retinoid activity. In humans, the CPABPII gene encodes the synthesis of cellular retinoic acid-binding protein. As such, expression of the CRABPII gene is directly related to and strongly correlated with retinoid efficacy. The inventors have found that the presence of NFκB-inhibitor in a composition containing a retinoid improves or potentiates the beneficial effects of retinoid as measured by CRAPB II expression.

The degree of synergy shown in CRAPBII expression, "% Synergy," for a particular combination of retinoid and NFκB-inhibitor can be determined using the CRAPBII EXPRESSSION TEST. The CRAPBII EXPRESSSION TEST is conducted in the following manner. One centimeter-diameter ex vivo skin explants are prepared from skin abdominal biopsy after plastic surgery. The skin explants are maintained in KGM Gold™ culture medium supplemented with amphotericinB, 0.125 μg/ml at 37° C., in a water saturated atmosphere for the 48 hour duration of the test. The explants are placed in a conventional test plate, epidermal surface oriented up, and in sufficient culture medium to nearly but not completely immerse the sample (i.e., the epidermal surface protrudes from the upper surface of the medium). Test composition is applied to the epidermal surface protruding from the culture medium. After 48 hours, using conventional techniques known to those skilled in the art, the explants are removed, from which epidermal mRNA is extracted and expression of CPABPII gene is measured by Quantitative real time PCR (QRT-PCR) using a suitable sequence of oligonucleotides.

A water-in-oil emulsion base containing the desired retinoid is used for the test composition. The NFκB-Inhibitor may optionally be included in the test composition or mixed separately into the culture medium. For instance, depending on the relative penetration rate of the NFκB-Inhibitor, it may be desirable to include it in the test composition or the culture medium to eliminate penetration rate as a variable in the test. If contained in the culture medium, the NFκB-Inhibitor need not penetrate into the epidermis from the protruding epidermal surface, but rather may penetrate the epidermis from the underlying culture medium. If the NFκB-Inhibitor is included in the test composition, the NFκB-Inhibitor must penetrate into the epidermis from the protruding epidermal surface.

The concentration of water in the test composition can be adjusted to accommodate sufficient levels of retinol (and NFκB-Inhibitor, if present in the test composition). An example of a suitable oil-in water emulsion base that may be used for the test composition is shown in Table 1 below:

TABLE 1

Suitable Oil-In Water Emulsion Base for CRAPBII EXPRESSSION TEST

| Tradename | INCI | Concentration (wt. percent) |
|---|---|---|
| Water, Demineralized | Water | 83.4 |
| Carbopol Ultrez 10 | Carbomer | 0.4 |
| Edeta BD chelating agent | Disodium EDTA | 0.1 |
| Nipagin M | Methylparaben | 0.2 |
| Propylparaben | Propylparaben | 0.15 |
| Phenoxyethanol | Phenoxyethanol | 0.5 |
| Sodium Hydroxide | Sodium Hydroxide | 0.1 |
| Simulsol 165 | PEG-100 Stearate; Glyceryl Stearate | 2.0 |
| Nipanox BHT | BHT | 0.1 |
| Lanette 16 | Cetyl Alcohol; Stearyl Alcohol; Myristyl Alcohol | 1.0 |
| DUB ININ | Isononyl Isononanoate | 7.0 |
| Propylene Glycol | Propylene Glycol | 5.0 |
| Ascorbic Acid Crystalline | Ascorbic acid | 0.05 |

The CRAPBII expression is determined (i) individually for a given amount of retinoid, (ii) individually for a given amount of NFκB-Inhibitor, and (iii) for a mixture of the retinoid at amount (i) and the NFκB-Inhibitor at amount (ii). The % Synergy is calculated with the formula below:

$$\% \text{ Synergy} = 100\% \times [[CRAPBII_{mixture} / (CRAPBII_{retinoid} + CRAPBII_{NF\kappa B-Inhibitor})] - 1]$$

While the concentration of NFκB-Inhibitor may be selected to provide at least about 15% synergistic CRABPII expression for the composition of the invention, in certain embodiments, the level of NFκB-Inhibitor may be selected to provide a higher level of synergy, such as at least about 50%, or at least about 80% synergy, in CRABPII expression.

The concentration of NFκB-Inhibitor may, in one embodiment, be selected, for example, using the results of the NFκB-INHIBITION TEST. For example, one may estimate a suitable concentration by performing the NFκB-INHIBITION TEST at several (e.g., 4 or more) concentrations, as shown in Example 1 below. The concentration of NFκB-Inhibitor may be selected, for example, so as to provide a Percent NFκB Inhibition of at least about 35%, preferably at least about 55%, more preferably at least about 70%, most preferably at least about 90%, when tested at a concentration of 10 micrograms per milliliter. This concentration of NFκB-Inhibitor may be combined in the composition with no more than about 0.075% by weight retinoid and % Synergy in CRAPBII expression determined, as shown in Example 2 below.

The inventors have observed that, in certain embodiments, synergy in CRAPBII expression can surprisingly be observed at not only a low concentration of retinoid (no more than about 0.075% by weight), but also low concentrations of NFκB-Inhibitor. This is advantageous, since the concentration of retinoid can be maintained at a low level, avoiding possible negative irritation side effects of the retinoid, while obtaining a potent boost in efficacy from the NFκB-Inhibitor.

In certain embodiments of the invention, the composition includes no more than about 0.075% by weight of a retinoid, such as retinol, and no more than about 0.5% by weight of an NFκB-Inhibitor. In a preferred embodiment, the composition includes no more than about 0.075% of a retinoid and about 0.1% to about 0.5% of an NFκB-Inhibitor.

Topical Compositions

The compositions of the present invention are applied topically to human skin and/or hair. In addition to the NFκB-inhibitor and retinoid, the composition further includes a cosmetically acceptable topical carrier that may be from about 50% to about 99.99%, by weight, of the composition (e.g., from about 80% to about 99.9%, by weight, of the composition). In a preferred embodiment of the invention, the cosmetically-acceptable topical carrier is or includes water. The cosmetically-acceptable topical carrier may include one or more ingredients selected from the group consisting of wetting agents, emollients, oils, humectants, and the like. In one embodiment, the cosmetically-acceptable topical carrier is or includes a substrate such as a non-woven fabric or film material.

The compositions may be made into a wide variety of product types that include but are not limited to lotions, creams, gels, sticks, sprays, ointments, cleansing liquid washes and solid bars, shampoos, pastes, foams, powders, mousses, shaving creams, wipes, patches, hydrogels, film-forming products, facial masks and skin masks, films and make-up such as foundations, and mascaras. These product types may contain several types of cosmetically acceptable topical carriers including, but not limited to solutions, suspensions, emulsions such as microemulsions and nanoemulsions, gels, solids and liposomes.

The compositions useful in the present invention can be formulated as solutions. Solutions typically include an aqueous or organic solvent (e.g., from about 50% to about 99.99% or from about 90% to about 99% of a cosmetically acceptable aqueous or organic solvent). Examples of suitable organic solvents include propylene glycol, polyethylene glycol (200-600), polypropylene glycol (425-2025), glycerol, 1,2,4-butanetriol, sorbitol esters, 1,2,6-hexanetriol, ethanol, and mixtures thereof.

Compositions useful in the subject invention may be formulated as a solution comprising an emollient. Such compositions preferably contain from about 2% to about 50% of an emollient(s). As used herein, "emollients" refer to materials used for the prevention or relief of dryness, such as by preventing the transepidermal loss of water from the skin. Examples of emollients include, but are not limited to vegetable oils, mineral oils, fatty esters, and the like.

A lotion can be made from such a solution. Lotions typically contain from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically contains from about 5% to about 50% (e.g., from about 10% to about 20%) of an emollient(s) and from about 45% to about 85% (e.g., from about 50% to about 75%) of water.

Although it is preferred that the composition of the present invention includes water, the composition may alternatively be anhydrous or an ointment that includes no water but organic and/or silicone solvents, oils, lipids and waxes. An ointment may contain a simple base of animal or vegetable oils or semi-solid hydrocarbons. An ointment may contain from about 2% to about 10% of an emollient(s) plus from about 0.1% to about 2% of a thickening agent(s).

The composition may be formulated as an emulsion. If the topical carrier is an emulsion, from about 1% to about 10% (e.g., from about 2% to about 5%) of the topical carrier contains an emulsifier(s). Emulsifiers may be nonionic, anionic or cationic. Examples of suitable emulsifiers include those typically identified as such in the art of personal care and cosmetic formulations.

Lotions and creams can be formulated as emulsions. Typically such lotions contain from 0.5% to about 5% of an emulsifier(s). Such creams typically contain from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the cosmetic art and are useful in the subject invention. Multiphase emulsion compositions, such as the water-in-oil-in-water type or the oil-in-water-in-oil type, are also useful in the subject invention. In general, such single or multiphase emulsions contain water, emollients, and emulsifiers as essential ingredients.

The compositions of this invention can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically contains between about 0.1% and 5%, by weight, of such gelling agents.

The compositions of the present invention can also be formulated into a solid formulation (e.g., a wax-based stick, soap bar composition, powder, or a wipe containing powder).

The compositions useful in the subject invention may contain, in addition to the aforementioned components, a wide variety of additional oil-soluble materials and/or water-soluble materials conventionally used in compositions for use on skin and hair, at their art-established levels.

Additional Cosmetically Active Agents

In one embodiment, the composition further contains another cosmetically active agent. As used herein, a "cosmetically active agent" is a compound (e.g., a synthetic compound or a compound isolated from a natural source or a natural extract) that has a cosmetic or therapeutic effect on the skin or hair, including, but not limiting to, anti-acne agents, shine control agents, anti-inflammatory agents (non-NFκB Inhibiting), anti-mycotic agents, anti-parasite agents, external analgesics, sunscreens, photoprotectors, antioxidants, keratolytic agents, surfactants, moisturizers, nutrients, vitamins, energy enhancers, anti-perspiration agents, astringents, deodorants, firming agents, anti-callous agents, and agents for hair and/or skin conditioning.

In one embodiment, the agent is selected from, but not limited to, the group consisting of hydroxy acids, benzoyl peroxide, D-panthenol, octyl methoxycinnimate, titanium dioxide, octyl salicylate, homosalate, avobenzone, carotenoids, free radical scavengers, spin traps, amines (e.g., neutrol), ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper such as Cu:Gly-His-Lys, coenzyme Q10, peptides, amino acids such as proline, vitamins, lactobionic acid, acetyl-coenzyme A, niacin, riboflavin, thiamin, ribose, electron transporters such as NADH and FADH2, and other botanical extracts such as aloe vera, feverfew, oatmeal and derivatives and mixtures thereof. The cosmetically active agent will typically be present in the composition of the invention in an amount of from about 0.001% to about 20% by weight of the composition, e.g., about 0.005% to about 10% such as about 0.01% to about 5%.

Examples of vitamins include, but are not limited to, vitamin Bs such as vitamin B3, vitamin B5, and vitamin B 12, vitamin C, vitamin K, and different forms of vitamin E like alpha, beta, gamma or delta tocopherols or their mixtures, and derivatives thereof.

Examples of hydroxy acids include, but are not limited, to glycolic acid, lactic acid, malic acid, salicylic acid, citric acid, and tartaric acid.

Examples of antioxidants include, but are not limited to, water-soluble antioxidants such as sulfhydryl compounds and their derivatives (e.g., sodium metabisulfite and N-acetylcysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, tocopherols (e.g., tocopherol acetate), tocotrienols, and ubiquinone. Natural extracts containing antioxidants suitable for use in the compositions of this invention, include, but are not limited to, extracts containing flavonoids and isoflavonoids and their derivatives (e.g., genistein and diadzein), extracts containing resveratrol and the like. Examples of such natural extracts include grape seed, green tea, pine bark, and propolis.

Other Materials

Various other materials may also be present in the composition, as known in the art. These include humectants, pH adjusters, chelating agents (e.g., EDTA), fragrances, dyes, and preservatives (e.g., parabens) such as those commonly used in cosmetic formulations The composition and formulations and products containing such compositions of the present invention may be prepared using methodology that is well known by an artisan of ordinary skill.

Methods of Use

Compositions of the present invention may be topically applied to mammalian skin that is in need of treatment for improvement of one or more signs of skin aging or acne as described above. In one embodiment, the compositions are applied to skin in need of improvement in firmness, texture, or the appearance of lines and wrinkles. The compositions may be applied to the skin in need of such treatment according to a suitable treatment regimen, e.g., from as much as, twice per day to as little as once every three days or so.

In certain embodiments, compositions of the present invention may also be useful for treating other need states associated with skin. For example, compositions of the present invention may be useful for treating post-inflammatory hyperpigmentation, for reducing pore size, for reducing sebum production, and for scar mitigation. In certain other embodiments, compositions of the present invention may be applied simultaneously with or within several hours of a mechanical or physical exfoliant such as a microdermabrasion treatment, or with a chemical exfoliant or keratolytic agent such as salicylic acid. In certain other embodiments, compositions of the present invention are applied to mild wounds or post-surgical sites to facilitate healing.

It is believed that one skilled in the art can, based upon the description herein, utilize the present invention to its fullest extent. The following specific embodiments are to be construed as merely illustrative, and not limitative of the remainder of the disclosure in any way whatsoever. The following non-limiting examples further illustrate the invention.

Example 1

NFκB-Inhibition

The NFκB-INHIBITION TEST described above was performed on test samples of Bay 11-7082 (Sigma-Aldrich, St. Louis, Mo.), Tetrahydrocurcuminoids CG (Sabinsa Corporation, Piscataway, N.J.), as well as various concentrations of 4-hexylresorcinol. The results are shown in Table 2, in which NF-κB Gene Reporter Activation (Luminescence, L) is reported for the test samples and a control sample. Percent NF-κB Inhibition is also reported.

TABLE 2

Results of NFκB-INHIBITION TEST

|  | NF-kB Gene Reporter Activation (Luminescence, L) | Percent NF-kB Inhibition |
| --- | --- | --- |
| Untreated | 1.2 ± 0.3 | — |
| TNFα (100 ng/ml) Stimulated, "L$_{control}$" | 108.2 ± 8.5 | — |

TABLE 2-continued

Results of NFκB-INHIBITION TEST

|  | NF-kB Gene Reporter Activation (Luminescence, L) | Percent NF-kB Inhibition |
| --- | --- | --- |
| TNFα + 4-Hexylresorcinol (50 μg/ml) | 9.3 ± 0.9 | 91.4% |
| TNFα + 4-Hexylresorcinol (10 μg/ml) | 29.3 ± 9.2 | 72.9% |
| TNFα + 4-Hexylresorcinol (5 μg/ml) | 55.1 ± 1.7 | 50.9% |
| TNFα + 4-Hexylresorcinol (1 μg/ml) | 106.1 ± 1.9 | 1.9% |
| TNFα + Tetrahydrocurcuminoids CG (10 μg/ml) | 37.8 ± 2.6 | 65.1% |
| Bay 11-7082 (25 μM) | 11.3 ± 5.6 | 89.5% |

Bay 11-7082, Tetrahydrocurcuminoids CG and 4-hexylresorcinol showed strong NF-κB inhibition.

Example 2

4-Hexylresorcinol and Retinol—Expression of CRAPBII

The CRAPBII EXPRESSSION TEST as described above was performed on a series of test compositions containing retinol, 4-hexyresorcinol, or combinations of both of these compounds. For this series of tests, the oil-in water-emulsion base described in Table 1 was used. Retinol and/or 4-hexyresorcinol were both included in the water-in-oil emulsion base. Values for CRAPBII expression are reported in Table 3 below. For combinations, the % Synergy, calculated as described above, is also reported.

TABLE 3

CRAPBII EXPRESSION

| Example | Retinol (Wt. %) | 4-Hexyl-resorcinol (Wt. %) | CRABPII Expression | % Synergy |
| --- | --- | --- | --- | --- |
| Comp. 1 | 0.04 | 0 | 193 | — |
| Comp. 2 | 0.075 | 0 | 322 | — |
| Comp. 3 | 0.1 | 0 | 498 | — |
| Comp. 4 | 0 | 0.5 | 4 | — |
| Comp. 5 | 0 | 1 | 27 | — |
| Ex. 1 | 0.04 | 0.5 | 387 | 96 |
| Ex. 2 | 0.075 | 0.5 | 550 | 69 |
| Ex. 3 | 0.04 | 1 | 232 | 5 |
| Ex. 4 | 0.075 | 1 | 414 | 19 |
| Comp. 8 | 0.1 | 1 | 225 | −57 |

As shown in Table 3, CRAPBII expression is positively correlated to and quite sensitive to concentration of retinol over the tested range. 4-hexylresorcinol used at low amounts generally improved the CRAPBII expression, while higher amounts of 4-hexylresorcinol generally reduced CRAPBII expression. Synergistic response was surprisingly observed when the concentration of retinol was no more than about 0.075% by weight of the composition. Furthermore, the synergy was greatly magnified when the concentration of 4-hexylresorcinol was about 0.5% by weight (approximately 50 ng/ml).

Example 3

Bay 11-7082 and Retinol—Expression of CRAPBII

The CRAPBII EXPRESSSION TEST was performed for a series of test compositions containing retinol, Bay 11-7082, or combinations of both. For this series of tests, the oil-in water-emulsion base shown below in Table 4 was used to make the remainder of the test compositions.

TABLE 4

Oil-In Water Emulsion Base

| Ingredient | Concentration (wt. percent) |
|---|---|
| Aqua | 55.7123 |
| Ammonium Acryloyldimethyltaurate/VP | 0.5 |
| Disodium EDTA | 0.1 |
| Glycerin | 5.0 |
| Butylene Glycol | 2.0 |
| PEG-8 | 5.0 |
| Cetaryl alcohol: Ceteareth-20 | 3.0 |
| Stearyl Alcohol; Ceteareth-20 | 3.0 |
| Ethylhexyl Methoxycinnamate | 2.0 |
| Isohexadecane | 1.5 |
| PPG-15 Stearyl Ether; BHT | 4.5 |
| Pentaerythrityl Tetraethylhexanoate | 7.0 |
| *Butyrospermum Parkii* (Shea Butter) | 1.0 |
| Tocopheryl Acetate | 0.25 |
| BHT | 0.1 |
| Dimethicone | 2.0 |
| Cyclohexasiloxane; Cyclopentasiloxane | 2.01 |
| Polyacrylamide; C13-14 Isoparaffin; Laureth-7 | 2.0 |
| Nylon-12 | 3.0 |
| Ascorbic Acid | 0.05 |
| Citric Acid | 0.25 |
| Sodium Hydroxide | 0.0277 |

For this series of tests, retinol was included in the test composition. However, Bay 11-7082 was not included in water-in-oil emulsion base, but rather was included in the culture medium. CRAPBII expression is reported in Table 5 below. For combinations, the % Synergy is also reported.

TABLE 5

CRAPBII EXPRESSION

| Example | Retinol (Wt. %) | Bay 11-7082 (μM) | CRABPII Expression | % Synergy |
|---|---|---|---|---|
| Comp. 9 | 0.04 | 0 | 324 | — |
| Comp. 10 | 0 | 1 | 84 | — |
| Comp. 11 | 0 | 10 | 115 | — |
| Ex. 5 | 0.04 | 1 | 631 | 54 |
| Ex. 6 | 0.04 | 10 | 347 | −21 |

As shown in Table 5, CRAPBII expression was found to be synergistic for combinations of retinol with the NF-κB inhibitor Bay 11-7082. While the combination of 0.04% retinol with 1 μM of BAY 11-7082 showed synergistic CRAPBII expression, no synergy was observed for the combination of 0.04% retinol with 10 μM of Bay 11-7082.

The data demonstrates that the combination of an NF-κB inhibitor and a retinoid in a composition wherein the retinoid is present in a concentration of no more than about 0.075% by weight of the composition produces a surprising and synergistic increase in retinol activity.

I claim:

1. A method of treating mammalian skin, comprising applying to said skin a composition comprising a retinoid, 4-hexyl resorcinol, and a cosmetically-acceptable topical carrier, wherein the amount of retinoid in the composition is no more than 0.075% by weight of the composition and the amount of 4-hexyl resorcinol is no more than about 0.5% by weight of the composition.

2. The method of claim 1, wherein said skin is in need of improvement in a sign of skin aging.

3. The method of claim 2, wherein said skin is in need of improvement in firmness, texture, the appearance of lines or wrinkles, or the loss of elasticity.

4. The method of claim 1, wherein said skin is in need of improvement in a sign of acne.

5. The method of claim 4, wherein said skin comprises blemishes, lesions, or pimples, pre-emergent pimples, blackheads, and/or whiteheads.

* * * * *